(12) United States Patent
Ujihira

(10) Patent No.: US 11,642,148 B2
(45) Date of Patent: May 9, 2023

(54) MINIMALLY-INVASIVE SURGERY EQUIPMENT

(71) Applicants: Kosuke Ujihira, Okayama (JP); Nikkotech,co,Ltd., Okayama (JP)

(72) Inventor: Kosuke Ujihira, Okayama (JP)

(73) Assignees: KOSUKE UJIHIRA, Okayama (JP); NIKKOTECH CO., LTD., Okayama (JP)

( * ) Notice: Subject to any disclaimer, the term of this patent is extended or adjusted under 35 U.S.C. 154(b) by 0 days.

(21) Appl. No.: 17/593,043

(22) PCT Filed: May 14, 2019

(86) PCT No.: PCT/JP2019/019031
§ 371 (c)(1),
(2) Date: Jan. 25, 2022

(87) PCT Pub. No.: WO2020/183740
PCT Pub. Date: Sep. 17, 2020

(65) Prior Publication Data
US 2022/0142664 A1 May 12, 2022

Related U.S. Application Data

(60) Provisional application No. 62/817,462, filed on Mar. 12, 2019.

(51) Int. Cl.
*A61B 17/29* (2006.01)
*A61B 17/00* (2006.01)
(52) U.S. Cl.
CPC ........ *A61B 17/29* (2013.01); *A61B 2017/003* (2013.01); *A61B 2017/2908* (2013.01); *A61B 2017/2929* (2013.01)

(58) Field of Classification Search
CPC .............. A61B 17/29; A61B 2017/003; A61B 2017/00305; A61B 2017/00318; A61B 2017/2908; A61B 2017/2929
See application file for complete search history.

(56) References Cited

U.S. PATENT DOCUMENTS 5,522,788 A * 6/1996 Kuzmak .......... A61B 17/00234
606/190
2003/0036748 A1 2/2003 Cooper et al.
(Continued)

FOREIGN PATENT DOCUMENTS

CA 2640029 A1 4/2009
CN 104284637 A 1/2015
(Continued)

OTHER PUBLICATIONS

International Search Report for International application No. PCT/JP2019/019031.
(Continued)

*Primary Examiner* — Ashley L Fishback
(74) *Attorney, Agent, or Firm* — Taro Yaguchi

(57) ABSTRACT

A minimally invasive surgical device characterized by comprising: a manipulable handle (2) manipulated by a user inside a body cavity, a treatment part (3) that holds a specific swappable surgical instrument that is inserted into the body cavity and manipulated using the manipulable part, and a linking part (4), provided between the manipulable handle and the treatment part, for disposing the surgical instrument held by the treatment part in a desired orientation at a desired position within the body cavity. The linking part comprising: two or more connecting parts (7a, 7b, 8a, 8b) that are connected in series in the longitudinal direction of the linking part, and form a joint (7, 8) that enables rotation around the longitudinal axis or an axis orthogonal to the longitudinal axis; and a linking part control mechanism that
(Continued)

moves the two or more connecting parts toward or away from each other to open or constrict the angle of the joint around the longitudinal axis and/or the angle thereof around an axis orthogonal to the longitudinal axis, thereby disposing the treatment part at the desired position and in the desired orientation within the body cavity.

12 Claims, 10 Drawing Sheets

(56) References Cited

U.S. PATENT DOCUMENTS

| | | |
|---|---|---|
| 2006/0178556 A1 | 8/2006 | Hasser et al. |
| 2006/0199999 A1 | 9/2006 | Ikeda et al. |
| 2009/0088792 A1 | 4/2009 | Hoell, Jr. et al. |
| 2010/0228284 A1 | 9/2010 | Cooper et al. |
| 2011/0028991 A1 | 2/2011 | Ikeda et al. |
| 2012/0220831 A1 | 8/2012 | Cooper et al. |
| 2014/0188091 A1 | 7/2014 | Vidal et al. |
| 2014/0200594 A1 | 7/2014 | Vidal et al. |
| 2015/0047451 A1* | 2/2015 | Kwon .................. A61B 17/29 74/490.05 |
| 2015/0066002 A1 | 3/2015 | Cooper et al. |
| 2015/0073436 A1 | 3/2015 | Inoue et al. |
| 2016/0249944 A1 | 9/2016 | Vidal et al. |
| 2017/0281296 A1 | 10/2017 | Cooper et al. |
| 2019/0046173 A1 | 2/2019 | Cooper et al. |

FOREIGN PATENT DOCUMENTS

| | | |
|---|---|---|
| EP | 2044893 A2 | 4/2009 |
| EP | 2338434 A2 | 6/2011 |
| EP | 2659853 A2 | 11/2013 |
| EP | 2851032 A1 | 3/2015 |
| JP | 2009-082705 A | 4/2009 |
| JP | 2010-505522 A | 2/2010 |
| JP | 2012-143589 A | 8/2012 |
| JP | 2013-208506 A | 10/2013 |
| JP | 2013-220108 A | 10/2013 |
| JP | 2013-240415 A | 12/2013 |
| JP | 2014-529436 A | 11/2014 |
| JP | 2017-189571 A | 10/2017 |
| WO | 2013-026920 A1 | 2/2013 |
| WO | 2013-026922 A1 | 2/2013 |
| WO | 2013172152 A1 | 11/2013 |

OTHER PUBLICATIONS

Office Action issued by the Japan Patent Office dated Apr. 6, 2021 for patent application No. JP2020-075866.
Second Office Action issued by the Japan Patent Office dated Jul. 6, 2021 for patent application No. JP2020-075866.

* cited by examiner

MINIMALLY-INVASIVE SURGERY EQUIPMENT

FIELD OF THE INVENTION

The present invention pertains to a surgical device that can be used in surgical procedures to treat lesions within body cavities with minimal invasiveness to the human body.

PRIOR ART

Recent years have seen increased usage of minimally invasive surgical procedures as typified by laparoscopic surgery and thoracoscopic surgery.

These minimally invasive surgical procedures have the advantage of involving smaller incisions and placing less of a burden upon the body than conventional surgical procedures in which large incisions are made in the body and surgical treatment is performed by direct vision. Daily advances in minimally invasive surgical procedures are made through improvements in the performance of endoscopes and surgical devices, and improvements in the procedures themselves.

Surgical devices used in common minimally invasive surgical procedures have a small-diameter insertable part that is inserted into a body cavity, and a handle for manually manipulating the insertable part. To use the surgical device, a small incision is first made in the chest, abdomen, etc., of a patient, and a surgical device insertion opening (port) is inserted into the incision. The insertable part of the surgical device is then inserted into a body cavity through the port. Forceps, scissors, an electric scalpel blade, or the like for performing surgical treatment is attached to the distal end of the body cavity insertable part, and controlled using the handle to perform the desired surgical procedure.

However, conventional minimally invasive surgical devices are difficult to use in the following cases, thus forcing the selection of a highly invasive procedure.

(1) Contact between devices, such as between devices held in both hands or between device and endoscope, or contact with vital organs is unavoidable due to highly constricted working space.

(2) An obstacle such as a vital organ or an adhesion is present between the handle and the target site, especially when there is little ability to move a vital organ or an adhesion covers a wide area.

(3) The handle and the target cannot be put in the same plane; for example, the handle and the target site are situated at diametrically opposite positions on either side of an immovable vital organ.

(4) The vector of the treatment performed on the target is not in the same plane as the handle and the target structure; one conceivable example is when an incision is made in the arterial wall of an artery running parallel to a line connecting two surgical device insertion openings (ports), not in the side closest to the operator, but in the side located 90° away therefrom in the clockwise direction around the centerline of the artery.

Conventional possible means of circumventing the problems described above include increasing the size of the wound in the surface of the body to increase working space, placing another port, moving a movable organ within the body cavity, and shifting to open-chest or open-abdomen surgery; however, all of these means increase invasiveness of the body.

Meanwhile, robotic surgeries have been developed in which a surgical robot capable of operating with an extremely high degree of freedom within bodily cavities is employed to solve the problems described above (for example see Patent Reference 1).

Surgical devices with joints provided in the distal end or shafts to increase the freedom of the surgical treatment part on the distal end of the device have also been developed to make it possible to circumvent the problems described above using conventional surgical devices (for example, see Patent Reference 2).

However, the conventional surgical robots disclosed in Patent Reference 1, while being increasingly widespread and having the advantages of extremely high freedom of operation and the ability to perform delicate movements, all have extremely complicated mechanisms and are quite expensive. Therefore, such robots cannot be easily adopted due to equipment-related or financial considerations. Moreover, it is difficult to obtain biofeedback, primarily tactile feedback, from a surgical treatment part equipped on a robot at current levels of technology, and a single surgical procedure incurs high material costs.

Surgical devices such as disclosed in Patent Reference 2 have shafts that are bendable or flexible, and enable surgical treatment parts to reach their targets through rolling movement of the entire device from the shaft onward. However, it is difficult to deform the shaft in three dimensions, or engage in extreme bending of 90° or more from the central axis of the handle, with the mechanism of Reference 2. Some underlying factors of this difficulty are the emphasis placed on the shaft being manipulable with one hand and being small in diameter in conventional surgical devices, and the fact that, in such conditions, free triaxial deformation and extreme bending of the shaft makes it impossible to maintain shaft rigidity and drastically complicates the structure of the device.

PRIOR ART REFERENCE

Patent Reference 1: JP 2012-143589 A
Patent Reference 2: JP 2017-189571 A

BRIEF SUMMARY OF THE INVENTION

Problem to be Solved by the Invention

The present invention was conceived in view of the problems described above, and has an object of providing a surgical device that is capable of bending and rotation in multiple directions while maintaining shaft rigidity and without increased structural complexity, and is capable of contributing a high degree of freedom to a distal end operating part comprising a surgical treatment part through anywhere from slight to extreme bending, or by maintaining complex three-dimensional shapes.

Means for Solving the Problem

In order to solve the problem described above, the present invention provides a first aspect as follows.
(1) A minimally invasive surgical device characterized by comprising:
a manipulable handle manipulated by a user inside a body cavity, a treatment part that holds a specific swappable surgical instrument that is inserted into the body cavity and manipulated using the manipulable part, and a linking part, provided between the manipulable handle and the treatment part, for disposing the surgical instrument held by the treatment part in a desired orientation at a desired position within the body cavity;

the linking part comprising:

two or more connecting parts that are connected in series in the longitudinal direction of the linking part, and form a joint that enables rotation around the longitudinal axis or an axis orthogonal to the longitudinal axis; and a linking part control mechanism that moves the two or more connecting parts toward or away from each other to open or constrict the angle of the joint around the longitudinal axis and/or the angle thereof around an axis orthogonal to the longitudinal axis, thereby disposing the treatment part at the desired position and in the desired orientation within the body cavity.

(2) The minimally invasive surgical device according to (1), wherein:

the linking part control mechanism comprises:

a linking part control slider that is capable of sliding in the longitudinal direction of the manipulable handle, and the movement of which can be locked at a specific position; and a flexible shaft member that is passed through the interior of the entirety of the linking part, and is affixed at one end to the treatment part and at another end to the linking part manipulation slider; and the linking part control slider is slid in the longitudinal direction of the manipulable handle to open or constrict the angle of the joint.

(3) The minimally invasive surgical device according to (1), wherein:

the linking part comprises a first joint that permits rotation around the longitudinal axis and/or a second joint that permits rotation around an axis orthogonal to the longitudinal axis.

(4) The minimally invasive surgical device according to (3), wherein:

the connecting parts comprise recessed parts and projecting parts that face and are capable of engaging with each other, and the recessed parts and the projecting parts are disengaged when released by the angle control part, and engaged at a fixed angle when constricted thereby.

(5) The minimally invasive surgical device according to (3), wherein:

the connecting parts have a stopper mechanism that restricts the angle of rotation thereof around the axis orthogonal to the longitudinal axis.

(6) The minimally invasive surgical device according to (5), wherein:

the restricted angle of rotation is ±30°.

(7) The minimally invasive surgical device according to (6), wherein:

the linking part comprises comprises a number of joints such that a 90°-180° bent shape can be maintained by a plurality of joints.

(8) The minimally invasive surgical device according to (1), wherein:

the linking part control slider is attached to a slide guider provided on the manipulable handle.

(9) The minimally invasive surgical device according to (8), wherein:

the shaft member is a tension-transmitting rod or wire; and the linking part control slider is a tension slider for adjusting the tension of the tension-transmitting rod.

(10) The minimally invasive surgical device according to (9), wherein:

the tension of the tension-transmitting rod or wire is adjusted by operating the linking part control slider parallel to the longitudinal direction of the handle.

(11) The minimally invasive surgical device according to (1), further comprising:

a surgical-treatment-part-controlling flexible shaft member that is connected at one end to the surgical treatment part, and the other end of which passed through the insides of the connecting parts and extends toward the handle; and a surgical treatment part actuation slider that is attached to the handle in a state of connection to the other end of the surgical-treatment-part-controlling flexible shaft member.

(12) The minimally invasive surgical device according to (11), wherein:

the surgical treatment part actuation slider is attached to the linking part control slider, and is movable with respect to the linking part control slider.

Other characteristics of the present invention will be made apparent in the descriptions of the embodiment of the present invention described below.

BEST MODE FOR EMBODYING THE INVENTION

An embodiment of the present invention will now be described with reference to the drawings.

(Overall Configuration)

Figure 1:
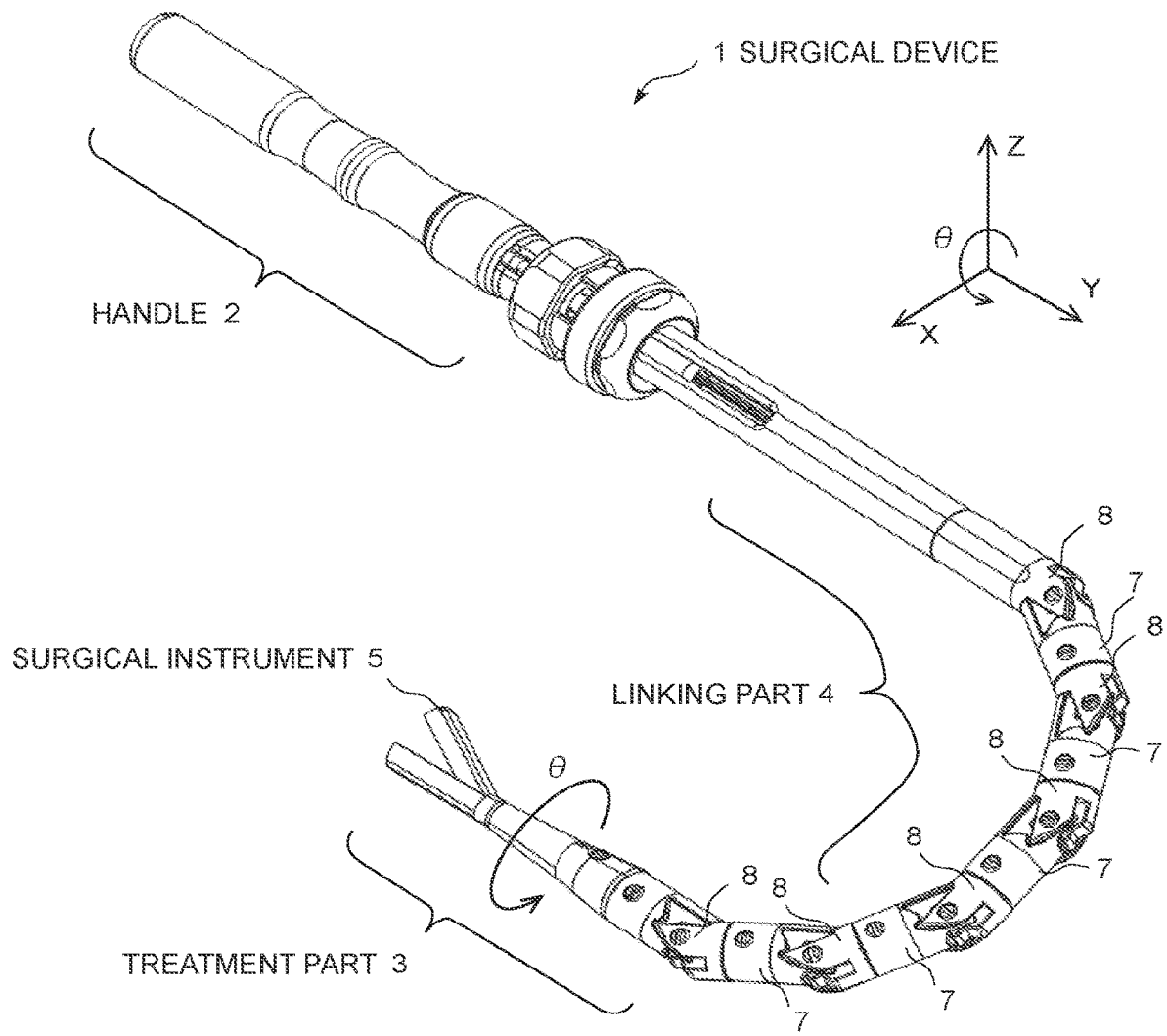
FIG. 1 is a schematic illustration of a minimally invasive surgical device according to an embodiment of the present invention.

FIG. 1 is an overall schematic illustration of a minimally invasive surgical device 1 according to this embodiment.

Broadly speaking, the surgical device 1 comprises a manipulable handle 2 for a user to manipulate the surgical device outside a body cavity, a treatment part 3 that holds a specific surgical instrument 5 that is inserted into a body cavity of a patient (not shown) and manipulated using the manipulable handle 2, and a linking part 4 that links the manipulable handle 2 and the treatment part 3 and disposes the surgical instrument 5 held by the treatment part 3 at a specific position within the body cavity.

Figure 2:
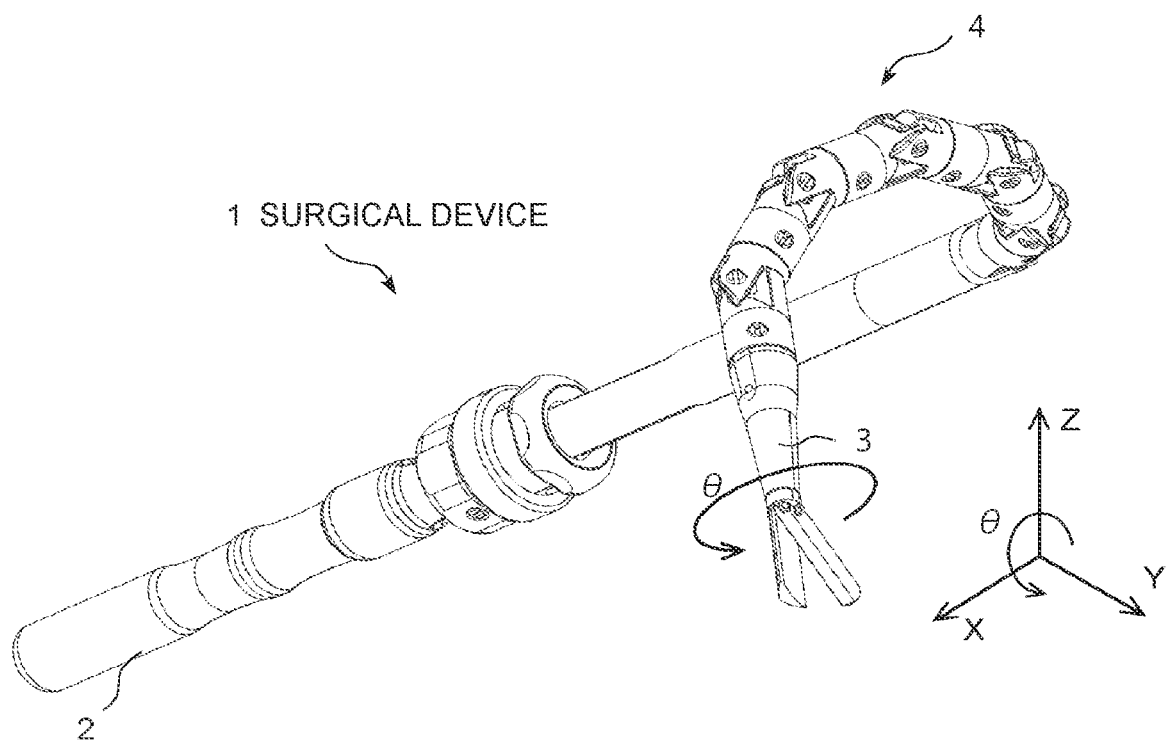
FIG. 2 is a schematic illustration showing the operation of the same.

FIGS. 1 and 2 depict states in which the linking part 4 is displaced to displace the position and direction of the treatment part 3 (surgical instrument 5) in three dimensions, i.e., in the XYZ directions, and in a rotational direction θ.

(Configuration of Linking Part)

The present invention is characterized by the configuration of the linking part 4 that realizes this three-dimensional displacement and positioning of the surgical instrument 5; this configuration will be described in detail below.

As shown in FIG. 1, the linking part 4 comprises two types of joint members 7, 8 disposed in a series in the longitudinal direction of the linking part 4, a plurality of the joint members being alternately linked in the order 7, 8, 7, 8, 7, 8, with joints being formed therebetween.

Figure 3:
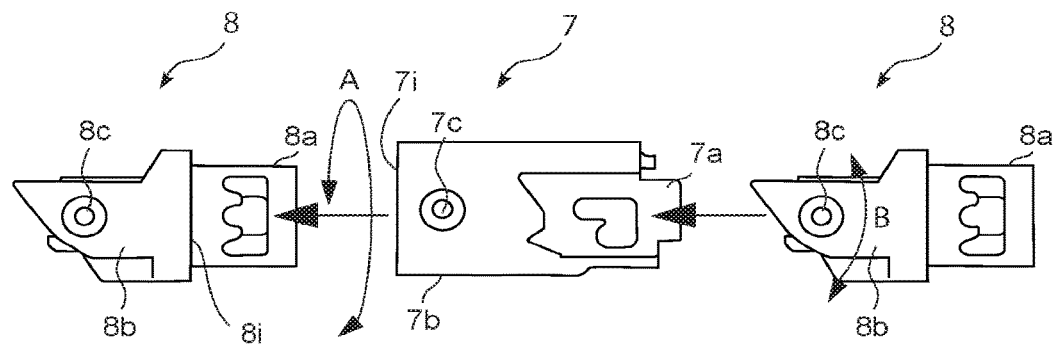
FIG. 3 is a schematic illustration of joint members in the same.

FIG. 3 is a magnified view of the link relationship between the two types of joint members (first joint member 7, second joint member 8), FIGS. 4(a)-(d) are a head-on view, top-down view, and side views of the first joint member 7, and FIGS. 5(a)-(d) are a head-on view, top-down view, and side views of the second joint member 8.

First, as shown by the link relationship in FIG. 3, the first joint member 7 and the second joint member 8 respectively comprise inner insertion parts 7a, 8a that are inserted into one of the joint members, and outer insertion parts 7b, 8b that receive the inserted inner insertion parts 7a, 8a of the counterpart member. The inner insertion parts 7a, 8a and outer insertion parts 7b, 8b respectively constitute the connecting parts of the present invention, and form the joints of the linking part 4 when connected.

Figure 5:
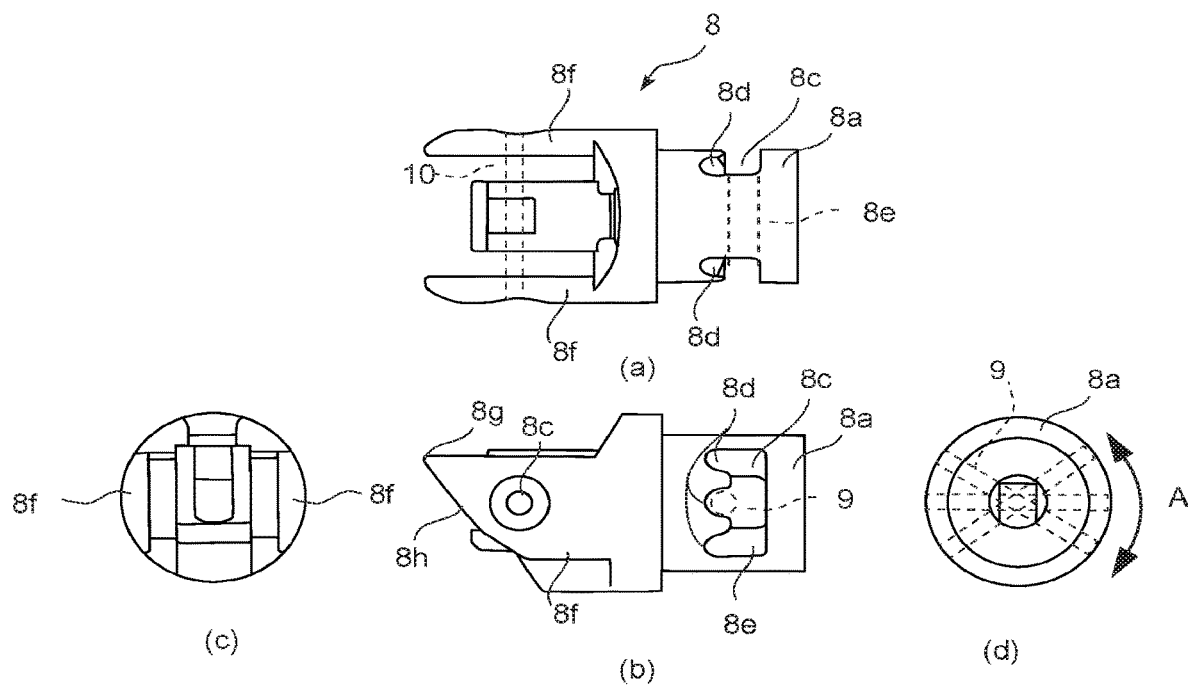
FIG. 5 is a schematic illustration of a second joint member in the same.
Figure 4:
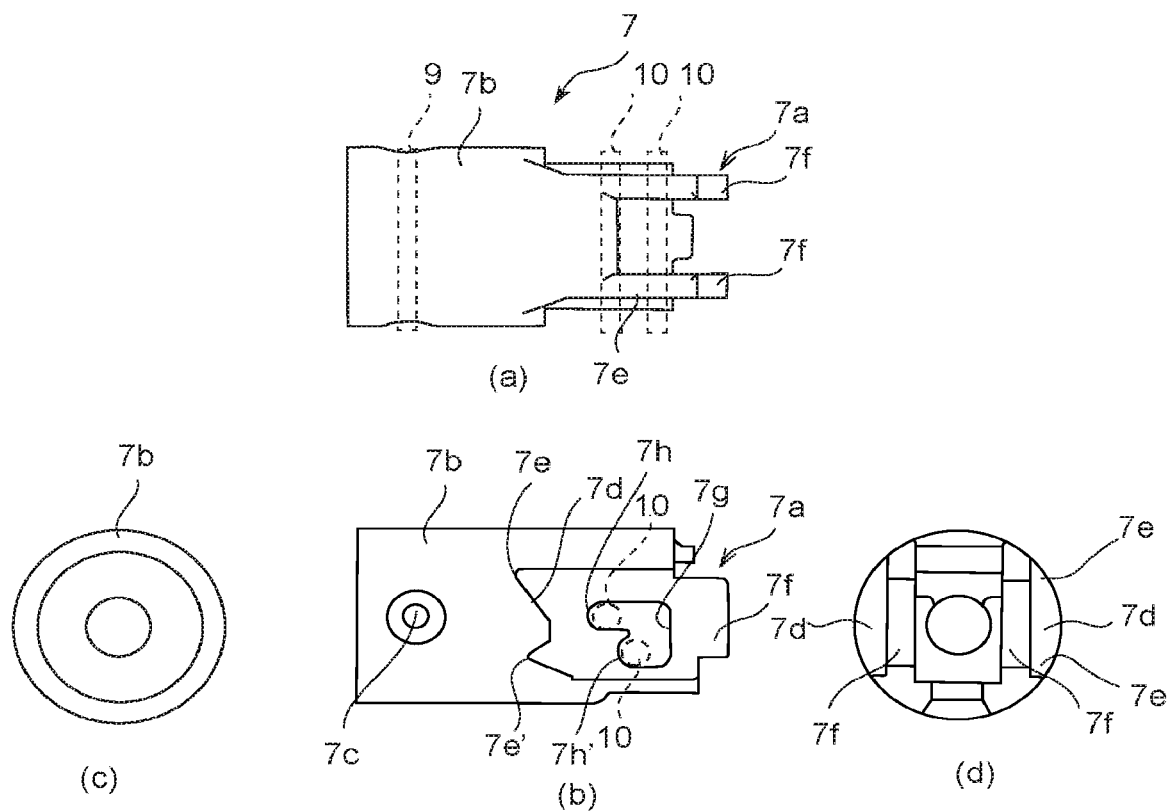
FIG. 4 is a schematic illustration of a first joint member in the same.

As shown in FIG. 4, the outer insertion part 7b of the first joint member 7 comprises a cylindrical-shaped retaining hole 7c for retaining a first linking pin 9 in the diameter direction. Meanwhile, as shown in FIG. 5, the inner insertion part 8a of the second joint member 8 inserted into the outer insertion part 7b of the first joint member 7 has a columnar shape that conforms to the inner diameter of the outer insertion part 7b of the first joint member 7, and comprises an engagement hole 8c that engages with the first linking pin 9, which is inserted into the outer insertion part 7b of the first joint member 7. The engagement hole 8c comprises one set of recessed parts 8d along the diameter direction, the recessed parts being provided at 30° intervals in the circumferential direction, and a linking passage 8e that links adjacent recessed parts 8d. The recessed parts 8d are configured to engage with the first linking pin 9 when the first and second joint members 7, 8 are actuated toward each other (in the direction indicated by the arrows in FIG. 3). The linking passage 8e is configured to disengage the first linking pin 9 and the recessed part 8d and permit the linking pin 9 to move between the recessed parts 8d when the first and second joint members 7, 8 are actuated away from each other (in the direction opposite that indicated by the arrows in FIG. 3).

Meanwhile, as shown in FIG. 5, the second joint member 8 comprises a pair of facing arms 8f, 8f that extend in the axial direction as the outer insertion part 8b. The distal ends of the pair of arms 8f comprises tapered parts 8g that engage with a guide face 7d and sunken parts 7e of the first joint member 7, to be described below, and sliding surfaces 8h that slide along the guide face 7d. The engagement holes 8c, which retain a second linking pin 10 that is suspended in a direction orthogonal to the central axis of the second joint member 8, are provided in the arms 8f.

As shown in FIG. 4, the first joint member 7 comprises a guide face 7d that contacts the arms 8f of the second joint member 8 and guides the arms 8f around the second linking pin 10 (in the direction indicated by arrow B) as the sliding faces 8h of the arms 8f slide therealong, and first and second sunken parts 7e, 7e' that engage with distal ends 8g of the arms 8f to fix the angle of rotation.

The inner insertion part 7a of the first joint member 7 comprises a center guide 7f that is inserted between the pair of arms 8f constituting the outer insertion part 8b of the second joint member 8, and the center guide 7f comprises a retaining hole 7g that retains the second linking pin 10 suspended between the pair of arms 8f.

The retaining hole 7g comprises first and second recessed parts 7h, 7h' that retain the second linking pin 10 attached to the second joint member 8 at positions at which the tapered parts 8g engage with the first sunken part 7e and the second sunken part 7e', respectively.

(Operation of Linking Part)

FIGS. 6(a) and (b) are schematic illustrations of the first and second joint members 7, 8 in an assembled form, and displacement thereof in the front-back direction.

As described above, with the central axes of the first and second joint members 7, 8 in alignment, the inner insertion parts 7a, 8a of one member are inserted into the outer insertion parts 7b, 8b of the other member to join the two, and inextricably linked by the first and second linking pins 9, 10. A linking part 4 comprising a plurality of joints is thus formed.

Meanwhile, a slide guide 12 and a slider 13 that can be slid along the slide guide 12 and positioned in the axial direction are attached to the manipulable handle 2. One end of a first actuation wire 14 shown in the drawing is affixed to the slider 13. The other end of the first actuation wire 14 passes through the linked first and second joint members 7, 8, as shown by the arrow in the drawing, and affixed to the rear end of the treatment part 3.

In this embodiment, a distal end 12a of the slide guide 12 is identical in shape to the outer insertion part 8b of the second joint member 8, and is linked by the second linking pin 10 to the rear end of the linking part 4 (the inner insertion part 7a of the first joint member 7).

A rear end 3a of the treatment part 3 is identical in shape to the inner insertion part 8a of the second joint member 8, and is linked by the first linking pin 9 to the distal end of the linking part 4.

The length to which the first actuation wire 14 is extended from the slider 13 can be controlled by adjusting the position at which the slider 13 and the first actuation wire 14 are joined. FIG. 6(a) depicts a state in which the slider 13 has been moved as far toward the distal end as possible, and FIG. 6(b) a state in which the slider 13 has been moved as far to the rear as possible.

The length to which the first actuation wire 14 is extended is adjusted to establish the gaps labeled 16, 17 in the drawing between the first and second joint members 7, 8 (the connecting parts of the present invention) in the state shown in FIG. 6(a), and to close the gaps 16, 17 between the first and second joint members 7, 8 in the state shown in FIG. 6(b).

Specifically, as shown in FIG. 3, a flange 8i is formed on the second joint member 8 between the inner insertion part 8a and the outer insertion part 8b, and, in the state shown in FIG. 6(a), the flanges 8i of the second joint members 8 and end surfaces 7i of the outer insertion parts 7b of the first joint members 7 are separated from each other to form the first gaps 16. In this state, the second joint members 8 are capable of rotating around their central axes, as indicated by A in FIGS. 3 and 5.

The slider 13 is moved rearward to create the state shown in FIG. 6(b), and the end surfaces 7i of the outer insertion parts 7b of the first joint members 7 are brought into contact with the flanges 8i of the second joint members 8 to close the first gaps 16, thereby restricting further axial movement of the joint members 7, 8, and the first linking pins 9 are engaged with the recessed parts 8*d* of the second joint members 8, thus also restricting rotating around the central axis.

Figure 6:
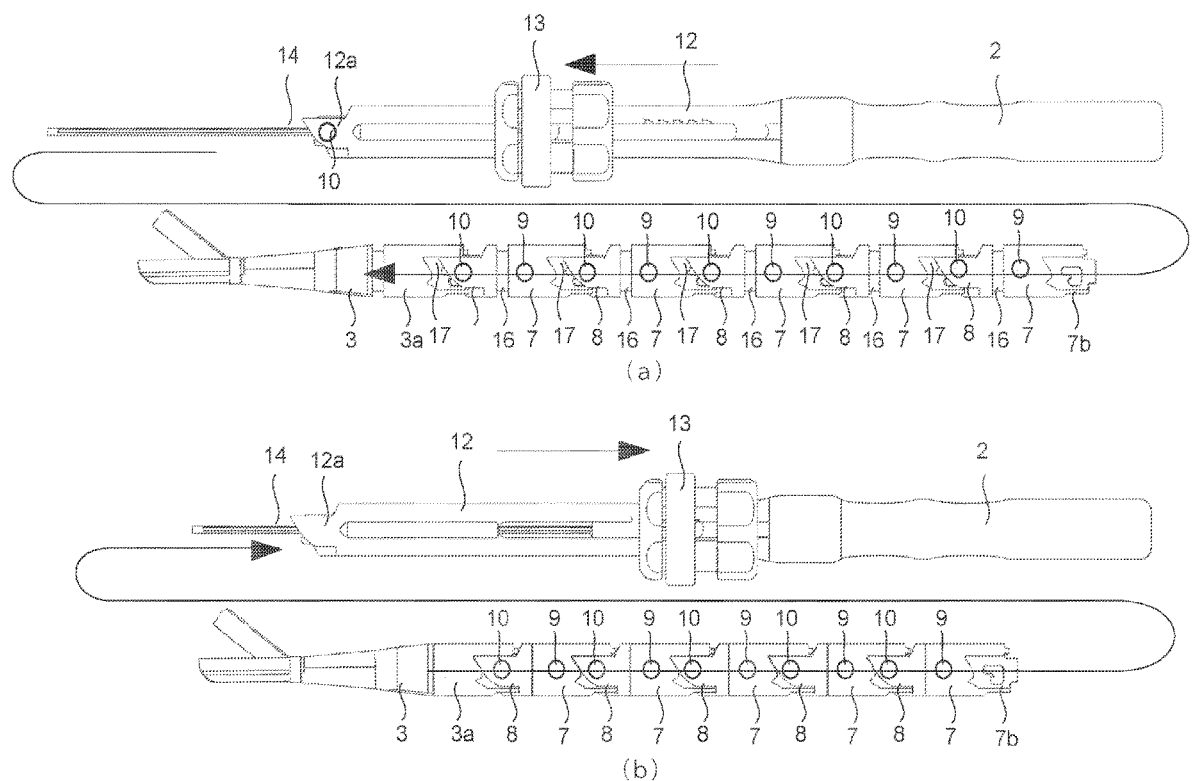
FIG. 6 is a schematic illustration of joint members in the same being manipulated.

The second gaps 17 shown in FIG. 6(*a*) are gaps between the sunken parts 7*e* formed in the first joint members 7 and the tapered parts 8*g* of the second joint members 8, and the first and second joint members 7, 8 are capable of rotating around each other in the direction indicated by arrow B in FIG. 3 when these second gaps 17 are present.

Sliding the slider 13 rearward to the state shown in FIG. 6(*b*) brings the second sunken parts 7*e* formed in the first joint members 7 into contact with the tapered parts 8*g* of the second joint members 8, resulting in a gap-free state. As a result, the first and second joint members are locked to each other, thereby restricting the rotation of each other.

This movement between the first and second joint members 7, 8 will be described below in greater detail with reference to FIG. 7.

Figure 7:
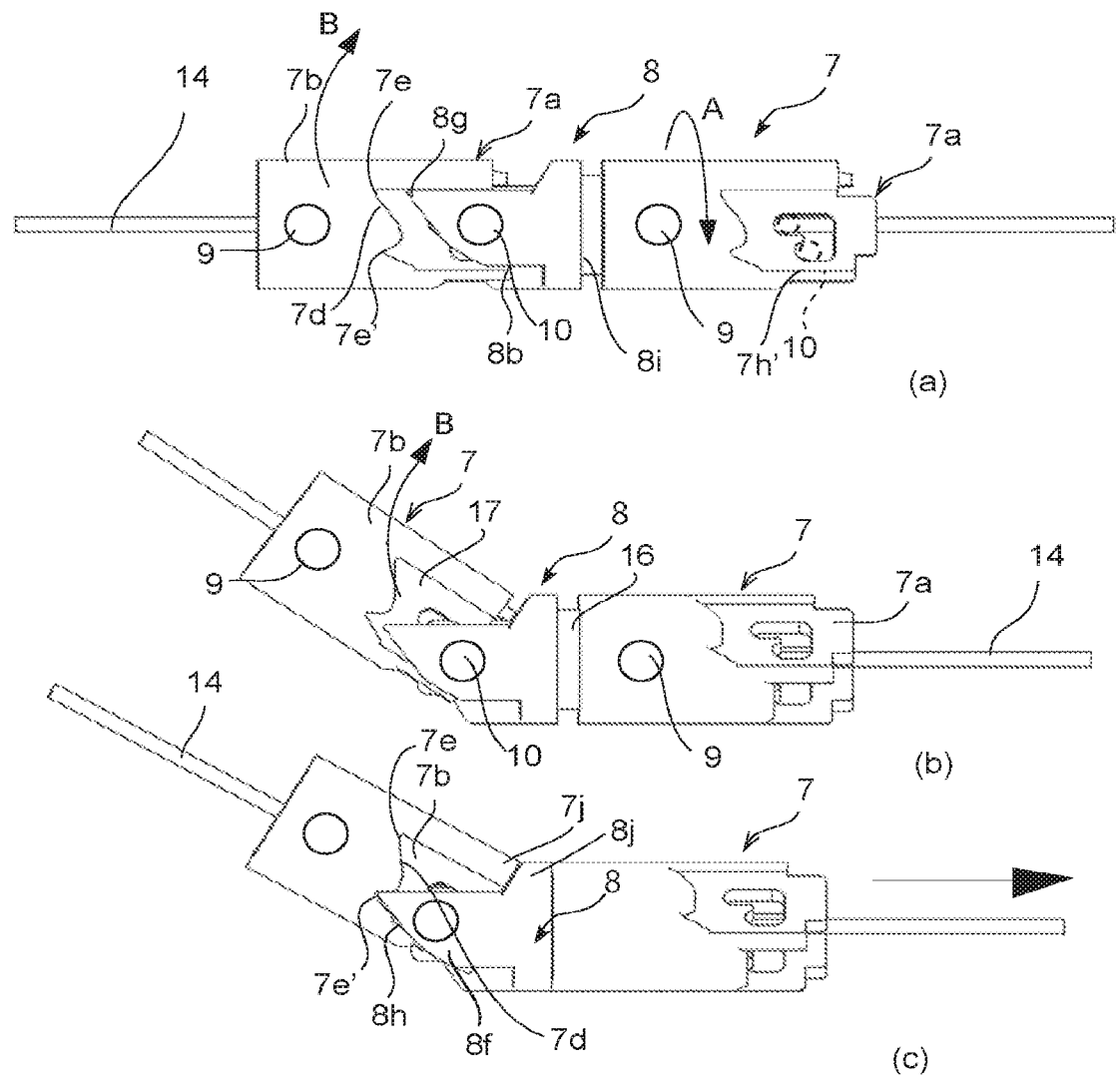
FIG. 7 is a schematic illustration showing the movement of first and second joints in the same.

In FIG. 7, an isolated section constituted by first joint members 7, 7 attached to the front and rear of a single second joint member 8 will be described.

FIGS. 7(*a*) and (*b*) depict the slider 13 positioned toward the distal end (the state shown in FIG. 6(*a*)), and FIG. 7(*c*) depicts the slider 13 having been moved toward the rear end (the state shown in FIG. 6(*b*)).

In the state shown in FIG. 7(*a*), the first joint member 7 attached to the front side of the second joint member 8 is capable of rotating around an axis orthogonal to the central axis, as indicated by arrow B. The first joint member 7 attached to the rear side of the second joint member 8 is capable of rotating around the central axis, as indicated by arrow A.

Simply sliding the slider 13 rearward from this state to close the gaps 16, 17 as described above yields the state shown in FIG. 6(*b*).

Meanwhile, FIG. 7(*b*) depicts a state in which the rear first joint member 7 has been rotated 30° around the central axis, and the front first joint member 7 has been rotated 30° around an axis orthogonal to the central axis.

In other words, the front first joint member 7 is capable of rotating to be positioned at two angles (0° and 30°) (direction indicated by arrow B) corresponding to the positions of the first and second sunken parts 7*e*, 7*e*'. The rear first joint member 7 is capable of rotating 0°, −30°, and +30° clockwise (the direction indicated by arrow A) in correspondence with the position of the recessed part 8*d*.

FIG. 7(*c*) depicts a state in which the slider 13 has been moved rearward from the state shown in FIG. 7(*b*). In the configuration of this example, the orientations of the first and second joint members 7, 8 are self-aligningly adjusted and fixed at a specific angle as the slider 13 is moved. In other words, the sliding faces 8*h* of the arms 8*f* of the second joint member 8 and the guide face 7*d* of the first joint member 7 slide between the first joint member 7 in front and the second joint member 8 in the center, and the tapered parts 8*g* thereof are guided to and engage with the sunken part 7*e*, thereby positioning the joint members. As a result, even if the angle between the first joint member 7 and the second joint member 8 deviates from the initial 30° or 0° (untilted), the members are guided by the sliding faces 8*h* and the guide parts 7*d* and are positioned and fixed at 30° or 0° when the second gap 17 is absent.

At this time, an upper edge 7*j* of the first joint member 7 and an upper edge 8*j* of the second linking pin 10 touch each other, and the second linking pin 10 engages with the recessed part 7*h* in the retaining hole 7*g*. As a result, the first joint member 7 and second joint member 8 are ultimately positioned and retained at three points, and the orientations thereof are kept in a highly rigid state even when tilted.

Meanwhile, the rear first joint member 7 and the second joint member 8 are positioned by the first linking pin 9 being guided to and engaging with one of the recessed parts 8*d* as the slider 13 is moved rearward. Thus, when the gaps 16, 17 are absent, the angles of the first and second joint members 7, 8 are fixed at 30°, 0°, and −30° in their respective rotational directions.

In this configuration, the first and second joint members 7, 8 are capable of respectively rotating around the central axis A and the axis B orthogonal to the central axis when the slider 13 is positioned to the front as shown in FIG. 6(*a*), thereby making it possible to freely deform the linking part 4 in the three-dimensional XYZ directions and the rotational direction θ around the central axis, as shown in FIGS. 1 and 2.

In other words, the orientation of the first and second joint members 7, 8 can be freely displaced in the state shown in FIG. 6(*a*), but the degree of displacement is restricted so that the linking pins 9, 10 do not disengage.

When the slider 13 is moved rearward from the state shown in FIG. 6(*a*) to the state shown in FIG. 6(*b*), the orientations of the first and second joint members 7, 8 are self-aligningly fixed at a specific angle as the gaps therebetween close, thereby fixing the shape of the freely deformed linking part 4.

Because the plurality of first and second joint members 7, 8 making up the linking part 4 are capable of being moved along the first actuation wire 14, it is possible to fix the rotational angles of some first and second joint members 7, 8 while adjusting the rotational angles of other first and second joint members 7, 8 to manifest a desired three-dimensional shape over the process of moving the slider 13. It is thus possible to set the general overall shape before moving the slider 13, then move the slider 13 to set the final shape.

(Configuration of Slider)

Next, the configuration and operation of the slider 13 will be described in more detail.

Figure 8:
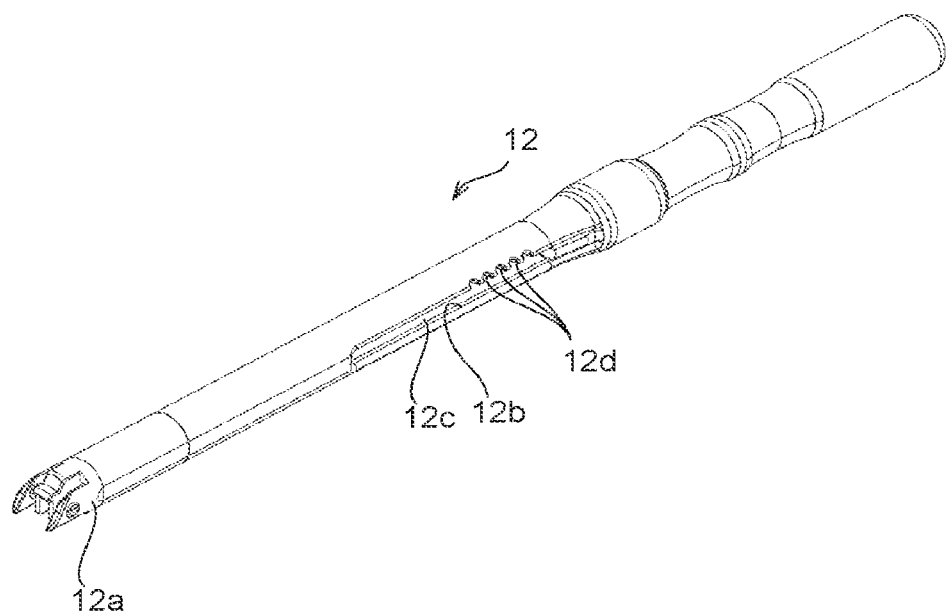
FIG. 8 is a schematic illustration of a slide guide.
Figure 9:
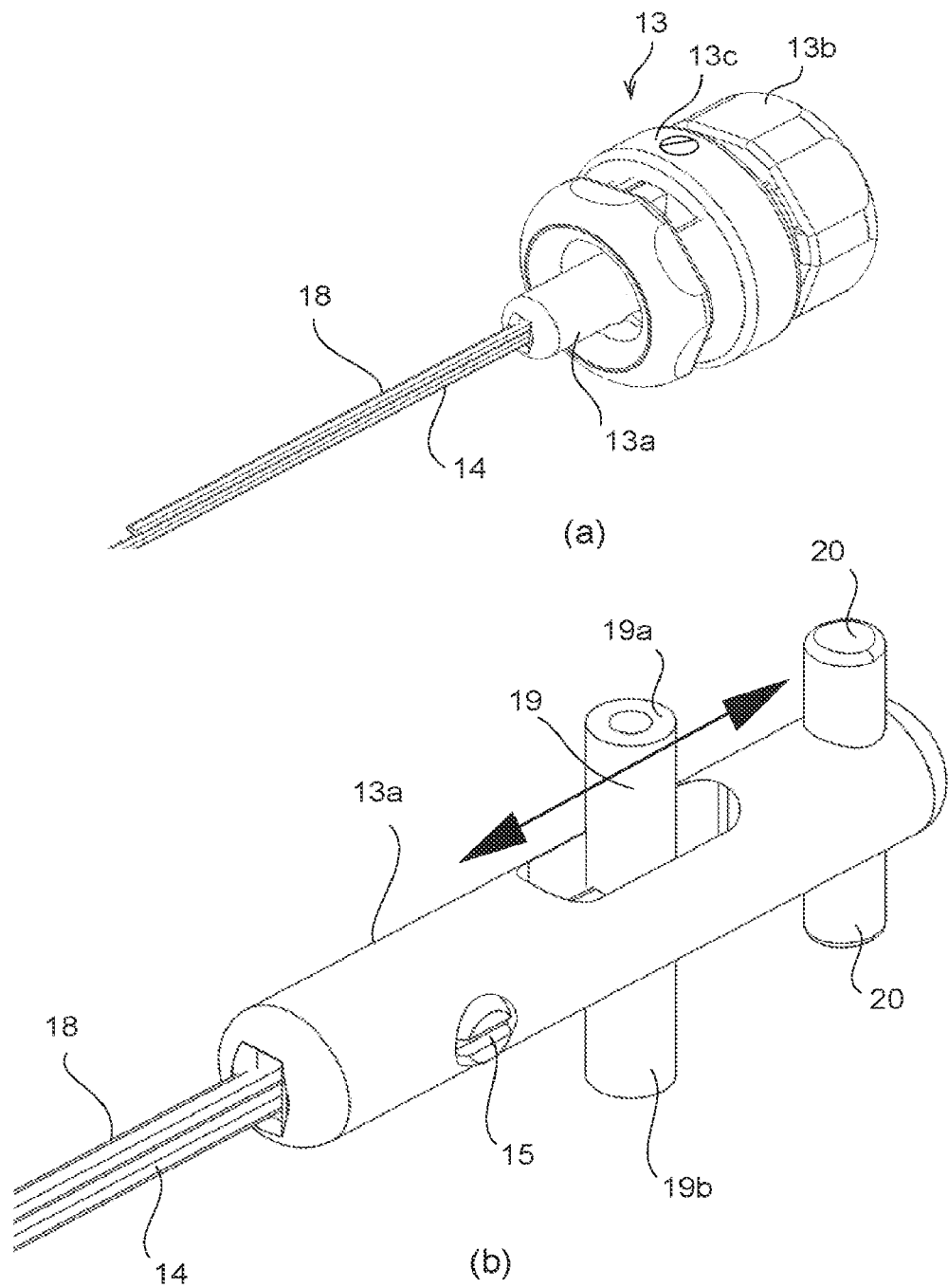
FIG. 9 is a schematic illustration of the configuration of a slider in the same.

FIG. 8 is a schematic view of the slide guide 12, and FIGS. 9(*a*), (*b*) are schematic views of the configuration of the slider 13 attached to the slide guide 12.

The slide guide 12 comprises a bore 12*b* provided along its central axis, a slit 12*c* that is provided in the bore 12*b* and opens onto the surface of the slide guide 12, and a plurality of cut-outs 12*d* formed in the slit 12*c* at specific intervals in the axial direction.

Meanwhile, the slider 13, as shown in FIG. 9(*a*), comprises a body 13*a* that is inserted in the bore 12*b* of the slide guide 12 (not shown in FIG. 9(*a*)) and capable of moving along the slide guide 12, and a manipulable handle 13*b* that is fitted on the outside of the slide guide 12 and affixed to the body 13*a*.

FIG. 9(*b*) depicts the body 13*a* alone. As seen in the drawing, the first actuation wire 14 for controlling the orientation of the linking part 4 as described above is affixed by a screw 15 to the front end of the body 13*a*. A separate second actuation wire 18 for controlling the surgical instrument 5 is inserted into the body 13*a*, and the second actuation wire 18 is attached to a surgical-instrument-controlling slider 19 attached to the body 13*a* so as to be capable of freely sliding forward and backward. Body projections 20 projecting outward in the axial direction are provided on the rear end of the body 13*a*.

To assemble the slider 13, the body 13a is first inserted into the bore 12b from one end of the slide guide 12, after which the manipulable handle 13b is fitted over the outside of the slide guide 12 and combined with the body 13a.

Figure 10:
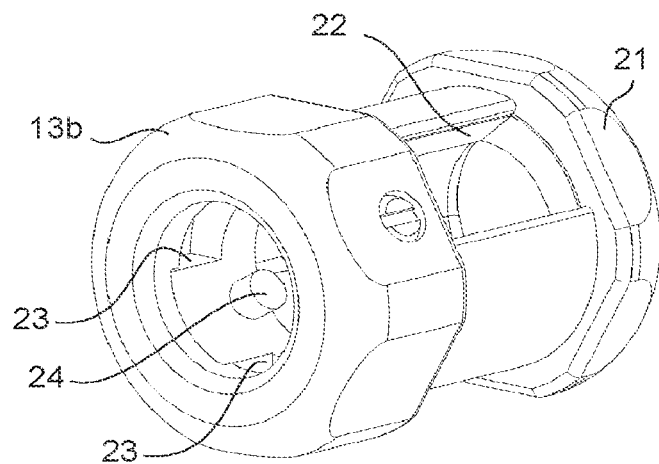
FIG. 10 is a schematic illustration of a manipulable handle of the same.

FIG. 10 is a perspective view of the manipulable handle 13b. Before assembly, a front end 21 of the slider is removed to open one end of a slit 22, and the handle is combined with the body 13a so that the slider 19 enters the slit 22. Cylindrical spaces 23 and a projection 24 projecting inward in the axial direction are provided inside the manipulable handle 13b. The projections 20 on the slider body 13a fit within the spaces 23 inside the handle, allowing the manipulable handle 13b to rotate around the central axis of the slide guide 12. The projection 24 inside the handle also rotates as the manipulable handle 13b rotates, and the projection 24 engages with the cut-outs 12d in the slide guide to immobilize the handle 13 with respect to the longitudinal direction.

Next, the ring-shaped member labeled 13c in FIG. 9(a) is attached to both ends 19a, 19b of the surgical-instrument-controlling slider 19. The ring 13c is a handle for manipulating the surgical-instrument-controlling slider 19.

Once the body 13a, manipulable handle 13b, and ring 13c have been combined in this way, the front end 21 of the slider is fixed in place to close the end of the slit 22.

The manipulable handle 13b engages with the body projections 20 in the spaces 23 inside the handle, and the manipulable handle 13b can be moved in the axial direction to move the body 13a in the same direction. Meanwhile, the manipulable handle 13b is capable of rotating around the central axis, but is restricted from rotating around the central axis of the body 13a by the body projections 20 fit into the slit 12c of the slide guide.

(Operation of Slider)

Figure 11:
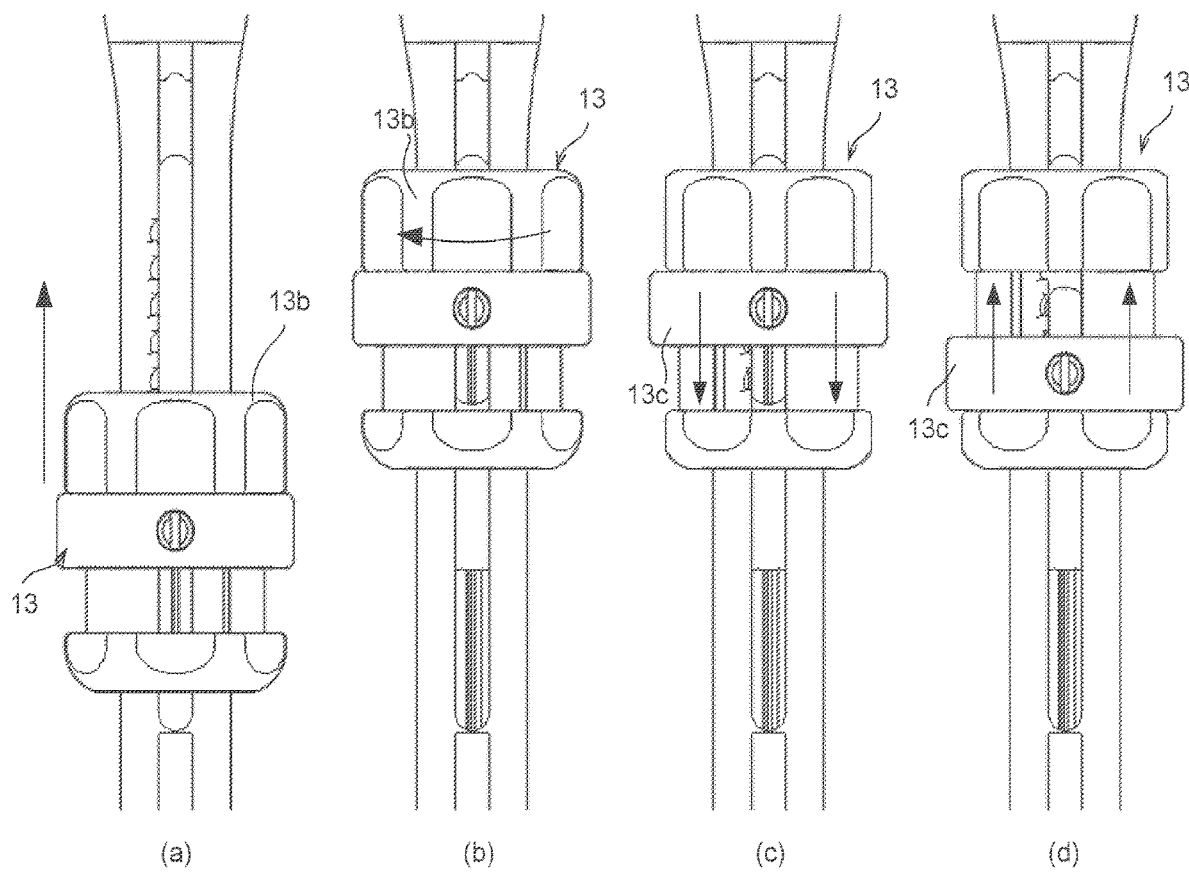
FIG. 11 is a schematic illustration demonstrating the manipulation of a manipulable handle and a ring of a slider.

Next, a method of manipulating the handle will be described with reference to FIG. 11.

FIG. 11(a), as described above, depicts a process of pulling the slider 13 rearward along the slide guide 12 while adjusting the rotational angles of the other first and second joint members 7, 8 to set the shape of the linking part 4 to a desired three-dimensional shape.

Once the linking part 4 has been successfully set to the desired shape, the manipulable handle 13b of the slider 13 is rotated to a specific angle around the axis, as shown in FIG. 11(b). As a result, the projection 24 (not shown) in the manipulable handle can engaged with the cut-outs 12d to immobilize the slider 13.

Next, FIGS. 11(c) and (d) depict the surgical instrument 5 being manipulated by manipulating the ring 13c to move the ring 13c relative to the slider 13. In this embodiment, the surgical instrument 5 is a pair of scissors (shown in FIG. 1), and the ring 13c can be moved forward as shown in FIG. 11(c) actuate the second actuation wire 18 forward and open the scissors. The ring 13c can also be moved rearward as shown in FIG. 11(d) to close the scissors via the second actuation wire 18.

In accordance with the configuration described above, the linking part 4 can be deformed in three dimensions, making it possible to obtain a surgical device that is capable, in particular, of extreme bending of 90° or more with respect to the central axis of the manipulable handle 2.

The present invention is not limited to the embodiment described above, and various modifications may be made thereto to the extent that they do not depart from the gist of the invention.

For example, while the number of joints formed by the first and second joint members 7, 8 is about 10 in the embodiment described above, this number can be freely set according to the required degree of freedom in and amount of three-dimensional deformation.

The expression "two or more connecting parts" in the claims refers to the "inner insertion part of one joint" and the "outer insertion part of another joint", and a pair of inner and outer insertion parts forms one relatively rotating joint. For example, in the example shown in FIG. 6(a), if the joint members 7, 8 were removed and the distal end 12a of the slide guide 12 were linked to the rear end 3a of the direct treatment part 3, the slide guide 12 and treatment part 3 would be linked by the "two or more linking parts" so as to be capable of being rotated and position around the linking pin, thereby forming a single joint. The present invention would be embodied even without the joint members 7, 8 as in the embodiment described above as long as there is at least one joint.

While the angles of rotation of the joints around the longitudinal axis and an axis orthogonal to the longitudinal axis is ±30° in the embodiment described above, the present invention is not limited thereto; for example, angles of ±40° can also be set.

By setting the number and possible angles of rotation of the joint members and joining parts in this way, it is possible to alter the range of motion of the joints according to the preferences of the surgeon or the specifics of the surgical procedure being performed.

For example, if the angle of rotation of joints formed by joining parts 7b and 8a around the longitudinal axis is ±30°, the range of motion will be ±60° if two joints are used, and ±180° if six are used. If not even one such joint is used, i.e., if only joints formed by joining parts 7a and 8b are used, rotation around the longitudinal axis will be impossible; however, such an arrangement is of course acceptable.

Meanwhile, if the angle of rotation of joints formed by joining parts 7a and 8b around an axis orthogonal to the longitudinal axis is ±30°, the range of motion will be ±60° if two joints are used, and ±180° if six are used. If not even one such joint is used, i.e., if only joints formed by joining parts 7b and 8a are used, rotation around axes orthogonal to the longitudinal axis will be impossible; however, such an arrangement is of course acceptable.

While a surgical treatment part capable of articulating motion, such as scissors, is used as an example of the surgical instrument in the embodiment described above, the present invention is not limited to such. For example, this surgical instrument can be swapped with a treatment part for which articulating motion is not required, such as a scalpel or retractor. In such cases, the second actuation wire 18 connected to the treatment part 3, and the handle actuating the wire, are unnecessary. In such cases, the ring 13c can be removed, or the manipulable handle can be replaced with one not provided with a ring in the first place.

REFERENCE NUMBERS

1: Minimally invasive surgical device
2: Manipulable handle
3: Treatment part
3a: Rear end
4: Linking part
5: Surgical instrument
7: First joint member
7a: Inner insertion part (one of the connecting parts of the present invention)
7b: Outer insertion part (one of the connecting parts of the present invention)

7c: Retaining hole
7d: Guide face
7e: First sunken part
7e': Second sunken part
7f: Center guide
7g: Retaining hole
7h: Recessed part
7i: End surface
7j: Upper edge
8: Second joint member
8a: Inner insertion part (one of the connecting parts of the present invention)
8b: Outer insertion part (one of the connecting parts of the present invention)
8c: Engagement hole
8d: Recessed part
8e: Linking passage
8f: Arm
8g: Tapered part
8h: Sliding face
8i: Flange
8j: Upper edge
9: First linking pin
10: Second linking pin
12: Slide guide
12a: Distal end
12b: Bore
12c: Slit
12d: Cut-out
13: Slider
13a: Body
13b: Manipulable handle
13c: Ring
14: First actuation wire
15: Screw
16: First gap
17: Second gap
18: Second actuation wire
19: Surgical instrument control slider
19a: One end
19b: One end
20: Body projection
21: Slider front end
22: Slit
23: Space inside handle
24: Projection inside handle

The invention claimed is:

1. A minimally invasive surgical device (1) that is facilitated to be inserted into a body cavity through a patient's skin incision to perform a specific surgical procedure characterized by comprising:
a manipulable handle (2) manipulated by a user outside the body cavity, a treatment part (3) that holds a specific swappable surgical instrument that is inserted into the body cavity and manipulated using the manipulable handle (2), and a linking part (4), provided between the manipulable handle (2) and the treatment part (3), for disposing the surgical instrument (5) held by the treatment part (3) in a desired orientation at a desired position within the body cavity;
the linking part (4) comprising:
two or more connecting parts (7, 8) that are connected in series in the longitudinal direction of the linking part (4) and held movable in a direction close to or apart from each other in a direction along a central axis with their central axes coinciding with each other,
wherein the two or more connecting parts (7, 8) constitute a joint that permits rotation around the central axis or around an axis orthogonal to the central axis by combining the two or more connecting parts (7, 8) with each other; and
a linking part control mechanism (13, 14) that constricts the angle of the joint around the central axis and/or the angle thereof around an axis orthogonal to the central axis by driving the two or more connecting parts (7, 8) in the direction of coming closer together from a position where they are separated from each other and engaging the connecting parts (7, 8), thereby disposing the treatment part (3) at the desired position and in the desired orientation within the body cavity
wherein, when the two or more connecting parts (7, 8) are separated from each other, the desired position and orientation of the treatment part are defined by displacement by the user holding an angle around the central axis of the joint or/and an angle around an axis orthogonal to the central axis and the position and orientation of the defined treatment part (3) is fixed by moving the connecting parts (7, 8) from the position where they are separated from each other to the direction where they are close together by the linking part control mechanism (13, 14).

2. The minimally invasive surgical device according to claim 1, wherein:
the linking part control mechanism comprises:
a linking part control slider that is capable of sliding in the longitudinal direction of the manipulable handle, and the movement of which can be locked at a specific position; and
a flexible shaft member that is passed through the interior of the entirety of the linking part along its central axis, and is affixed at one end to the treatment part and at another end to the linking part manipulation slider; and
the linking part control slider is slid in the longitudinal direction of the manipulable handle to open or constrict the angle of the joint.

3. The minimally invasive surgical device according to claim 2, wherein:
the linking part control slider is attached to a slide guider provided on the manipulable handle.

4. The minimally invasive surgical device according to claim 3, wherein:
the shaft member is a tension-transmitting rod or wire; and
the linking part control slider is a tension slider for adjusting the tension of the tension-transmitting rod.

5. The minimally invasive surgical device according to claim 4, wherein:
the tension of the tension-transmitting rod or wire is adjusted by operating the linking part control slider parallel to the longitudinal direction of the handle.

6. The minimally invasive surgical device according to claim 2, wherein:
further comprising:
a surgical-treatment-part-controlling flexible shaft member that is connected at one end to the surgical treatment part, and the other end of which passed through the insides of the connecting parts and extends toward the handle; and
a surgical treatment part actuation slider that is attached to the handle in a state of connection to the other end of the surgical-treatment-part-controlling flexible shaft member.

7. The minimally invasive surgical device according to claim 6, wherein:
the surgical treatment part actuation slider is attached to the linking part control slider, and is movable with respect to the linking part control slider.

8. The minimally invasive surgical device according to claim 1, wherein:
the linking part comprises a first joint that permits rotation around the longitudinal axis and/or a second joint that permits rotation around an axis orthogonal to the longitudinal axis.

9. The minimally invasive surgical device according to claim 8, wherein:
the connecting parts comprise recessed parts and projecting parts that face and are capable of engaging with each other, and the recessed parts and the projecting parts are disengaged when released by the angle control part, and engaged at a fixed angle when constricted thereby.

10. The minimally invasive surgical device according to claim 8, wherein:
the connecting parts have a stopper mechanism that restricts the angle of rotation thereof around the axis orthogonal to the longitudinal axis.

11. The minimally invasive surgical device according to claim 10, wherein:
the restricted angle of rotation is ±30°.

12. The minimally invasive surgical device according to claim 11, wherein:
the linking part comprises a number of joints such that a 90°-180° bent shape can be maintained by a plurality of joints.

* * * * *